United States Patent [19]

Gsell

[11] Patent Number: 4,918,088
[45] Date of Patent: Apr. 17, 1990

[54] PEST CONTROL

[75] Inventor: Laurenz Gsell, Basel, Switzerland

[73] Assignee: Ciba-Geigy Corporation, Ardsley, N.Y.

[21] Appl. No.: 218,190

[22] Filed: Jul. 13, 1988

[30] Foreign Application Priority Data

Jul. 20, 1987 [CH] Switzerland .................. 2747/87

[51] Int. Cl.[4] .......................................... A01N 43/40
[52] U.S. Cl. ..................................... 514/357; 546/333
[58] Field of Search ......................... 514/357; 546/333

[56] References Cited

U.S. PATENT DOCUMENTS 3,147,271 9/1964 Shapiro et al. ...................... 260/296

FOREIGN PATENT DOCUMENTS 235725 9/1987 European Pat. Off. .

OTHER PUBLICATIONS

Chem. Abst.: 108(3), 21897m (1988), Shiokawa et al.
Chemical Abstract, vol. 90 (1979), p. 608, #90: 87289f.

Primary Examiner—Douglas W. Robinson
Assistant Examiner—Zuhreh A. Fay
Attorney, Agent, or Firm—Kevin T. Mansfield

[57] ABSTRACT

The invention relates to the use of compounds of formula I

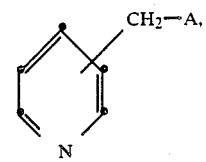

wherein A is a radical

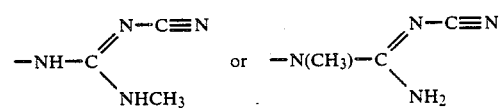

and tautomers thereof, for controlling noxious insects and pests of the order Acarina, and to compositions which contain these compounds. The compounds of formula I are particularly suitable for controlling noxious feeding and sucking insects.

17 Claims, No Drawings

PEST CONTROL

The present invention relates to the use of specific N-picolyl-N'-cyanoguanidine derivatives for controlling pests, and to pesticidal compositions which contain these compounds as active component.

Specifically, the invention relates to the use of a compound of formula I

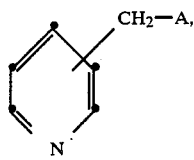

wherein A is a radical

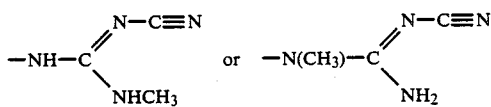

and tautomers thereof, for controlling noxious insects and pests of the order Acarina.

Thus in the practice of this invention, special reference is made to the use of compounds of formulae Ia and Ib:

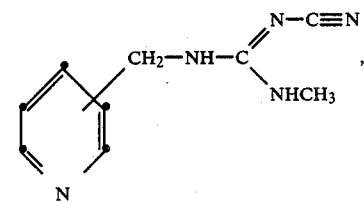

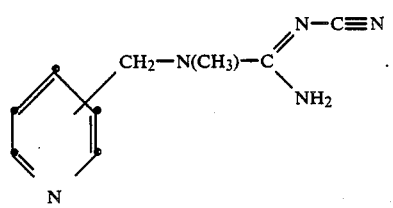

Within the scope of the utility of this invention, it is particularly preferred to use those compounds of formulae I, Ia and Ib, wherein the pyridyl radical is a pyrid-3-yl radical.

The invention further relates to novel compositions for controlling noxious insects and pests of the order Acarina, which compositions contain, as active component, at least one compound of formula I

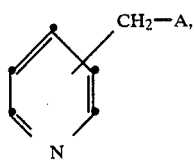

wherein A is a radical

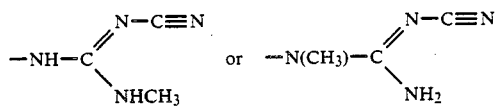

or a tautomer thereof, together with conventional adjuvants, carriers and diluents.

N-Picolyl-N-methyl-N'-cyanoguanidines which fall under formula I above, their preparation and the use thereof as intermediates for the synthesis of pharmaceuticals, have already been disclosed in U.S. patent specification No. 3 147 271. The preparation of pharmaceutically active N-picolyl-N'-methyl-N''-cyanoguanidines is also mentioned in C.A. Col. 90 (1979), 90: 87289 f.

Surprisingly, it has now been found that the compounds of formula I of this invention have excellent insecticidal and nematocidal properties while being well tolerated by plants and having low toxicity to warm-blooded animals. They are particularly suitable for controlling insects that attack plants and animals. In this connection attention is drawn to the very low toxicity of the compounds of this invention to fish.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina, in particular mites and ticks.

The good pesticidal activity of the compounds of this invention corresponds to a mortality of at least 50-60% of the above pests.

In addition to their action against mosquitos and flies, e.g. Aëdes aegypti and Musca domestica, the compounds of formula I are also suitable for controlling plant-destructive feeding insects in ornamentals and crops of useful plants, for example in cotton (e.g. against Spodoptera littoralis and Heliothis virescens) and in crops of cereals, fruits and vegetables (e.g. against Laspeyresia pomonella, Leptinotarsa decemlineata and Epilachna varivestis). The compounds of formula I are also very effective against larval insect stages and nymphs, especially of noxious feeding insects. In particular, the compounds of formula I can be used very successfully against plant-destructive cicadas, especially in rice crops. In this connection, the low toxicity to fish of the compounds of formula I merits special invention. Attention is also drawn to the fact that the compounds of formula I have a pronounced systemic as well as contact action against sucking insects, such as insects of the family Aphididae (for example Aphis fabae, Aphis craccivora, Aonidiella aurantii and Myzus persicae).

The following compounds which are disclosed in the aforementioned publications and which fall under the scope of formula I are particularly suitable for the purpose of this invention:

| Compound | | m.p. [°C.] |
|---|---|---|
| 1 | 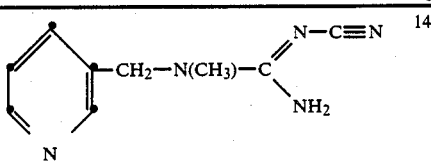 | 141–143 |
| 2 | 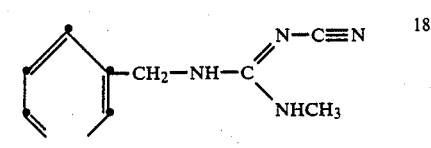 | 183–184 |
| 3 | 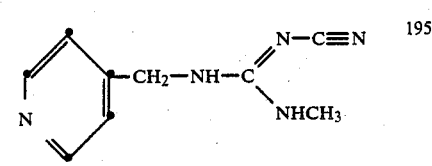 | 195–197.5 |

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and Bacillus thuringiensis preparations.

The compounds of formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand.

In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzylbis(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hauser Verlag, Munich/Vienna, 1981.

The pesticidal compositions usually contain—based on weight—0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration, for example from 0.1 to 1000 ppm.

The compositions may also contain further ingredients, such as stabilisers, antifoams, viscosity regulators, binders, tackifiers as well as fertilisers or other active ingredients for obtaining special effects.

EXAMPLE 1

Preparation of N-β-picolyl-N-methyl-N'-cyanoguanidine 7.3 g of dimethyl-N-cyanothioiminocarbonate and 6.1 g of β-picolylmethylamine are added to 20 ml of ethanol. NH$_3$ gas is then introduced into the mixture over 1 hour, whereupon en exothermic reaction (rise in temperature to 35° C.) takes place. The reaction mixture is then stirred for 1 hour and the methyl mercaptan formed is expelled completely by blowing N$_2$ gas into the mixture. The solvent is removed by distillation and the product is crystallised by addition of ether. The obtained title compound of formula

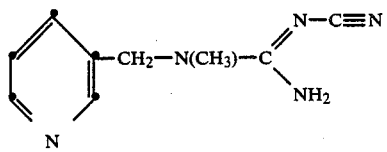

has a melting point of 141°-143° C. (compound 1).

EXAMPLE 2

Preparation of N-β-picolyl-N'-methyl-N''-cyanoguanidine

A mixture of 5.4 g of 3-picolylamine, 7.31 g of dimethyl N-cyanothioiminocarbonate and 50 g dimethylaminopyridine (as catalyst) in 50 ml of acetonitrile is kept under reflux for 2 hours. The batch is thereafter cooled to 5° C., and the crystals obtained are filtered with suction and washed with ether, affording N-cyano-S-methyl-N'-β-picolylisothiourea (m.p. 152°-154° C.). A mixture of βg of this compound, 3 g of 40% methylamine (in ethanol) and 50 ml of ethanol is kept for 16 hours under reflux, then cooled by pouring it on to a mixture of ice/sodium chloride, whereupon crystals of the title compound of formula

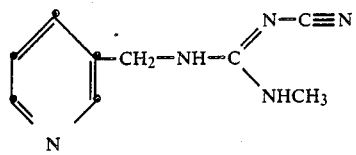

precipitate. The crystals are filtered with suction and have a melting point of 183°-184° C. (compound 2).

EXAMPLE 3

Formulations for compounds of formula I (throughout, percentages are by weight)

1. Wettable powders

|  | (a) | (b) | (c) |
|---|---|---|---|
| a compound of the Examples 1 or 2 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 67% | 27% | — |

The active compound is thoroughly mixed with the adjuvants and the mixture is thoroughly ground in a suitable mill, affording wettable powders which can be diluted with water to give suspensions of the desired concentration.

2. Emulsifiable concentrate

|  | (a) | (b) |
|---|---|---|
| a compound of the Examples 1 or 2 | 10% | 10% |
| octylphenol polyethlene glycol ether (4-5 mol of ethylene oxide) | 3% | — |
| calcium dodecylbenzenesulfonate | 3% | — |
| castor oil polyglycol ether (36 mol of ethylene oxide) | 4% | — |
| castor oil thioxilate | — | 25% |
| cyclohexanone | 30% | — |
| butanol | — | 15% |
| xylene mixture | 50% | — |
| ethyl acetate | — | 50% |

Emulsions of any required concentration can be obtained from this concentrate by dilution with water.

3. Dusts

|  | (a) | (b) |
|---|---|---|
| a compound of the Examples 1 or 2 | 5% | 8% |
| talcum | 95% | — |
| kaolin | — | 92% |

Ready-for-use dusts are obtained by mixing the active compound with the carrier, and grinding the mixture in a suitable mill.

4. Extruder granulate

| a compound of the Examples 1 or 2 | 10% |
| --- | --- |
| sodium lignosulfonate | 2% |
| carboxymethylcellulose | 1% |
| kaolin | 87% |

The active compound is mixed and ground with the adjuvants, and the mixture is subsequently moistened with water. The mixture is extruded and then dried in a stream of air.

5. Coated granulate

| a compound of the Examples 1 or 2 | 3% |
| --- | --- |
| polyethylene glycol (mol. wt. 200) | 3% |
| kaolin | 94% |

The finely ground active compound is uniformly applied, in a mixer, to the kaolin moistened with polyethylene glycol. Non-dusty coated granulates are obtained in this manner.

6. Suspension concentrate

| a compound of the Examples 1 or 2 | 40% |
| --- | --- |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active compound is intimately mixed with the adjuvants, giving a suspension concentrate from which suspensions of any desired concentration can be obtained by dilution with water.

EXAMPLE 4

Action against *Lucilia sericata* (larvae)

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of formula I are very effective against *Lucilia sericata*.

EXAMPLE 5

Action against *Aedes aegypti* (larvae)

A concentration of 400 ppm is obtained by pipetting a specific amount of a 0.1% solution of the test compound in acetone on to the surface of 150 ml of water in a beaker. After the acetone has evaporated, 30 to 40 two-day-old larvae of *Aedes aegypti* are put into the beaker containing the test compound. Mortality counts are made after 2 and 7 days.

Compounds of formula I are very effective in this test.

EXAMPLE 6

Insecticidal contact action against *Aphis craccivora*

Before the start of the test, 4- to 5-day old bean plants (*Vicia faba*) reared in pots are each populated with about 200 insects of the species *Aphis craccivora*. The treated plants are sprayed direct to drip point 24 hours later with an aqueous formulation containing 400 ppm of the test compound. Two plants are used for each test compound at the given concentration. A mortality count is made after 24 hours.

Compounds of formula I are very effective in this test.

EXAMPLE 7

Insecticidal systemic action against *Aphis craccivora* (in the soil)

Bean plants which have grown roots are transplanted into pots containing 600 ccm of soil. Then 50 ml of a formulation (prepared from a 25% wettable powder) of the test compound in a concentration of 400 ppm are poured direct onto the soil in the pots.

After 24 hours the growing parts of the plants are populated with aphids of the species *Aphis craccivora* and a plastic cylinder is then slipped over the plants to protect the aphids from any possible contact with the test substance either direct or via the gas phase.

A mortality count is made 48 and 72 hours respectively after the start of the test. Two plants, each in a separate pot, are used for each test substance at the given concentration. The test is carried out at 25° C. and about 70% relative humidity.

Compounds of formula I are very effective in this test.

EXAMPLE 8

Insecticidal contact action against *Myzus persicae*

Pea seedlings about 4 cm in height which have been reared in water are each populated with about 200 aphids of the species *Myzus persicae* before the start of the test. The treated plants are sprayed direct to drip point 24 hours later with an aqueous suspension containing the test compound in a concentration of 400 ppm. Two plants are used for each compound at the given concentration. A mortality count is made 48 hours after application. The test is carried out at 20°–22° C. and about 60% relative humidity.

The compounds of formula I are very effective in this test.

EXAMPLE 9

Insecticidal systemic action against *Myzus persicae*

Cabbage plants which have grown roots are transplanted in the 4- to 5-leaf stage into pots containing 60 ccm of soil. Then 50 ml of an aqueous formulation (prepared from a 25% wettable powder) of the test compound in a concentration of 400 ppm are poured direct on to the soil.

After 24 hours the growing parts of the plants are populated with aphids of the species *Myzus persicae* and plastic cylinders are then slipped over the plants to protect the aphids from any possible contact with the test substance either direct or via the gas phase.

The evaluation of percentage mortality is made 48 hours after the start of the test. Two plants, each in a separate pot, are used for each test substance at the given concentration. The test is carried out at about 25° C. and 60% relative humidity.

The compounds of formula I are very effective in this test.

EXAMPLE 10

Leaf penetration action against *Aphis craccivora*

A small shoot of Vicia faba, which is severely infested with aphids of the species *Aphis craccivora*, is placed in each of a number of 8 cm high plastic beakers (diameter about 6 cm). Each beaker is covered with a plastic lid having a punched opening of 2 cm diameter in the centre. A leaf of a *Vicia faba* plant is then placed over the opening in the lid without separating this leaf from the potted plant. The leaf is then fixed on the beaker with a second punched lid above the opening of the first lid. From underneath, i.e. through the opening of the first lid, the aphids in the beaker then infest the leaf of the plant used as bait. An aqueous formulation of the test compound is then applied in a concentration of 400 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds of formula I are very effective in this test.

EXAMPLE 11

Insecticidal systemic action against *Aphis craccivora* and *Myzus persicae* (in water)

Pea plantlets which have been infested with the aphids 24 hours before the start of the test are put into 20 ml of an aqueous mixture containing 400 ppm of the test compound. This aqueous mixture is prepared from an emulsifiable concentrate or a wettable powder formulation of the respective test compound and is contained in a beaker that is sealed with a plastic lid in which holes have been punched. The root of each infested plant is pushed through a hole in the lid into the mixture. The hole is then plugged with cotton wool to hold the plant fast and to protect it from contact with the gas phase of the mixture.

The test is carried out at 20° C. and 60% relative humidity. After 2 days a count is made of aphids which are no longer able to suck (comparison with untreated controls) in order to determine whether the test compound absorbed by the root is able to kill the aphids on the growing upper parts of the plants.

In the above test, compounds of formula I have a very good systemic action against insects of the species *Aphis craccivora*.

EXAMPLE 12

Stomach toxicant and contact action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 100 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

In this test, the compounds 1 and 2 effect 80-100% kill of *Nilaparvata lugens*.

EXAMPLE 13

Systemic action against *Nilaparvata lugens* (water)

Rice plants which are about 10 days old and about 10 cm high are put into a plastic beaker which contains 20 ml of an aqueous emulsion formulation of the test compound in a concentration of 100 ppm and which is sealed with a perforated plastic lid. The root of each rice plant is pushed through a hole in the plastic lid into the aqueous test formulation. The hole is then plugged with cotton wool to fix the plant and to exclude any contact with the gas phase of the test formulation. The rice plant is then populated with 20 nymphs of *Nilaparvata lugens* in the $N_2$-$N_3$ stage and covered with a plastic cylinder. The test is carried out at ca. 26° C. and 60% relative humidity with a period of light exposure of 16 hours. A mortality count is made 5 days later using untreated controls for comparison purposes, thereby establishing whether the test compound absorbed through the root kills the test organisms on the upper parts of the plant.

In this test compounds 1, 2 and 3 effect 80-100% kill of *Nilaparvata lugens*.

EXAMPLE 14

Stomach toxicant and contact action against feeding insects

Cotton plants about 25 cm high, in pots, are sprayed with aqueous emulsions which contain the test compound in a concentration of 800 ppm. After the spray coating has dried, the cotton plants are populated with *Spodoptera littoralis* and *Heliothis virescens* larvae in the $L_1$-stage. The test is carried out at 24° C. and about 60% relative humidity. The percentage mortality of the test insects is determined after 120 hours by making a comparison with untreated control insects.

Compounds of formula 1 are very effective against *Spodoptera larvae* in this test.

EXAMPLE 15

Action against *Nephotettix cincticeps* (nymphs)

The test is carried out with growing plants. Rice plants, about 20 days old and about 15 cm in height, are planted in pots having a diameter of 5.5 cm.

The plants are sprayed on a rotary table with 100 ml of an acetonic solution containing 400 ppm of test compound. After the spray coating has dried, the plants are populated with 20 nymphs of the test insects in the second or third stage. To prevent the cicadas from espcaing, a plexiglass cylinder is slipped over each plant and sealed with a gauze cover. The nymphs are kept for 5 days on each treated plant, which must be watered again at least once. The test is carried out at a temperature of about 23° C. at 55% relative humidity and with a light exposure period of 16 hours.

Compounds of formula I are very effective in this test.

What is claimed is:

1. A method of controlling insects and representatives of the order Acarina, which comprises contacting said pests, their different development stages or the locus thereof, with a pesticidally effective amount of a compound of formula I

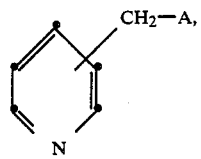   (I)

wherein A is a radical

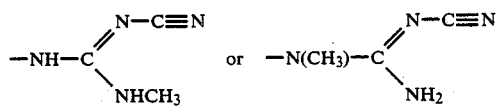

or a tautomer thereof, or with a composition containing such a compound.

2. The method of claim 1, wherein the compound is of formula Ia

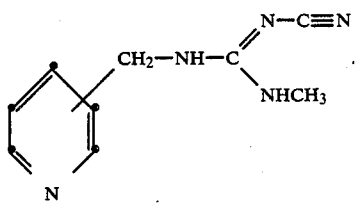   (Ia)

3. The method of claim 1, wherein the compound is of formula Ib

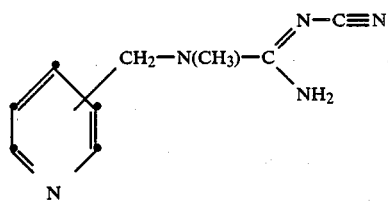   (Ib)

4. The method of claim 1, wherein the pyridyl radical is a pyrid-3-yl radical.

5. The method of claim 4, wherein the compound is of formula

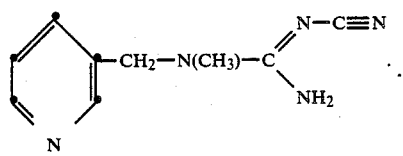

6. The method of claim 4, wherein the compound is of formula

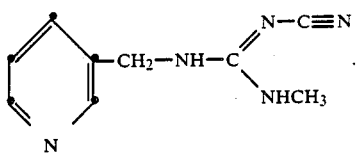

7. The method of claim 2, wherein the compound is of formula

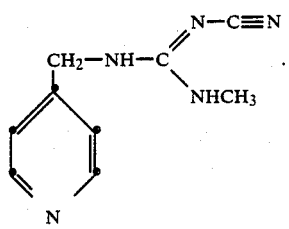

8. The method of claim 1, wherein the pests to be controlled are plant-destructive insects.

9. The method of claim 8, wherein the pests to be controlled are insects in rice crops.

10. A composition for controlling noxious insects and pests of the order Acarina, comprising as active component a pesticidally effective amount of a compound of formula I

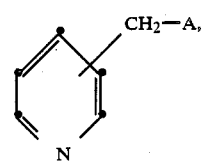   (I)

wherein A is a radical

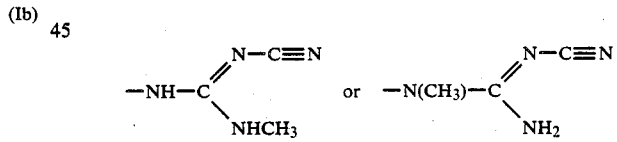

or a tautomer thereof together with an agriculturally acceptable carrier or other adjuvant.

11. A composition according to claim 10, which comprises a compound of formula Ia

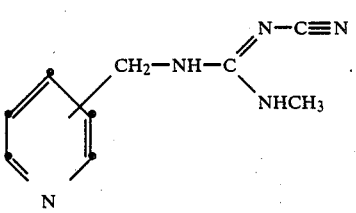   (Ia)

12. A composition according to claim 10, which comprises a compound of formula Ib

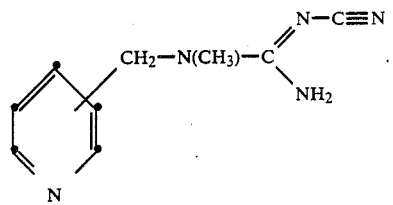  (Ib)

13. A composition according to claim 10, wherein the pyridyl radical is a pyridyl-3-yl radical.

14. A composition according to claim 13, which comprises the compound of formula

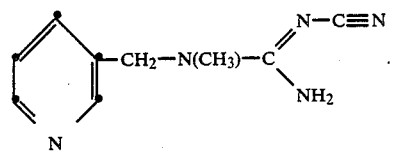

15. A composition according to claim 13, which comprises the compound of formula

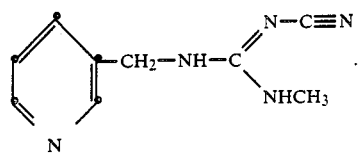

16. A composition according to claim 11, which comprises the compound of formula

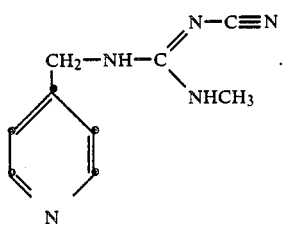

17. The method of claim 9, wherein the pests to be controlled are cicadas.

* * * * *